United States Patent
Reschke et al.

(10) Patent No.: US 6,932,090 B1
(45) Date of Patent: Aug. 23, 2005

(54) MOTION SICKNESS TREATMENT APPARATUS AND METHOD

(75) Inventors: Millard F. Reschke, LaPorte, TX (US); Jeffrey T. Somers, Houston, TX (US); George A. Ford, Webster, TX (US)

(73) Assignee: The United States of America as represented by the United States National Aeronautics and Space Administration, Washington, DC (US)

( * ) Notice: Subject to any disclaimer, the term of this patent is extended or adjusted under 35 U.S.C. 154(b) by 145 days.

(21) Appl. No.: 10/361,046

(22) Filed: Feb. 6, 2003

(51) Int. Cl.[7] ............................................. A61B 19/00
(52) U.S. Cl. ......................................... 128/898; 128/897
(58) Field of Search ................................ 128/897, 898

(56) References Cited

U.S. PATENT DOCUMENTS

| | | | |
|---|---|---|---|
| 4,929,228 A | 5/1990 | Hendricks | |
| 5,067,941 A | 11/1991 | Hendricks | |
| 5,276,539 A * | 1/1994 | Humphrey | 349/14 |
| 5,614,920 A * | 3/1997 | Coteus et al. | 345/7 |
| 5,647,835 A * | 7/1997 | Martineau | 600/27 |
| 5,829,446 A | 11/1998 | Tiffany | |
| 5,966,680 A * | 10/1999 | Butnaru | 702/150 |
| 6,097,450 A * | 8/2000 | Humphrey | 349/13 |
| 6,228,021 B1 | 5/2001 | Kania | |
| 6,275,998 B1 * | 8/2001 | Tromble | 2/449 |
| 6,493,154 B1 * | 12/2002 | Humphrey | 359/738 |
| 6,497,649 B2 * | 12/2002 | Parker et al. | 600/27 |
| 2001/0050754 A1 * | 12/2001 | Hay et al. | 351/213 |

OTHER PUBLICATIONS

Article "3-D Glasses—How They Work", 3D Gaming World, www.3dgw.com Copyright 1997, 1998, 1999, 2000, 5 pages.

"Motion Sickness Due to Vision . . . " G.M.Jones&G.Mandl, p. 303-311, Annals NY Academy Science 1981.

* cited by examiner

Primary Examiner—Samuel G. Gilbert
(74) Attorney, Agent, or Firm—Theodore U. Ro

(57) ABSTRACT

Methods and apparatus are disclosed for treating motion sickness. In a preferred embodiment a method of the invention comprises operating eyewear having shutter lenses to open said shutter lenses at a selected operating frequency ranging from within about 3 Hz to about 50 Hz. The shutter lenses are opened for a short duration at the selected operating frequency wherein the duration is selected to prevent retinal slip. The shutter lenses may be operated at a relatively slow frequency of about 4 Hz when the user is in passive activity such as riding in a boat or car or in limited motion situations in a spacecraft. The shutter lenses may be operated at faster frequencies related to motion of the user's head when the user is active.

34 Claims, 4 Drawing Sheets

MOTION SICKNESS TREATMENT APPARATUS AND METHOD

ORIGIN OF THE INVENTION

The invention described herein was made by employee(s) of the United States government and may be manufactured and used by or for the Government of the United States of America for governmental purpose without payment of any royalties thereon or therefore.

BACKGROUND OF THE INVENTION

1. Field of the Invention

The present invention relates generally to motion sickness management systems and, more specifically, to eyewear such as glasses or goggles for treating and/or preventing motion sickness.

2. Background of the Invention

Motion sickness is a well known malady that often occurs due to exposure to motion in the environment. Motion sickness is likely to occur on boats subject to rolling motion, space station activities, car travel, train travel, and the like. The symptoms may include vertigo or nausea. There is a wide variation between different individuals in sensitivity to motion sickness. Moreover for those persons affected, the symptoms can range from quite severe to minimal. There are various prior art theories as to the cause of motion sickness. Some of these theories are discussed hereinafter.

Traditional treatment for motion sickness has relied substantially on two primary methods: (1) adaptation, wherein individuals are repeatedly exposed to a motion environment known to induce sickness, or (2) drugs used to prevent the development of symptoms. Both methods have significant problems.

The adaptation method requires weeks (or even months) of exposure time to the provocative environment. Even after treatment, the individual may only be resistant to motion in that specific environment. For operation in microgravity environments, preflight adaptation may be effective for some individuals. However preflight adaptation requires a substantial investment in crew time and resources, and it is currently unknown about the effects of preflight adaptation during long duration flights. In-flight centrifugation of spacecraft or space stations may be the ultimate vestibular countermeasure, however, rapid implementation at this time is impracticable, will require significant amounts of time on-orbit to implement, and it is unlikely that centrifugation without visual-vestibular stimulation will succeed.

Drugs used for the treatment of motion sickness have significant side effects, e.g., drowsiness. Drugs can only be used in situations where these side effects are not a factor. For instance, persons who must be active or alert are not able to take such medications. Also, due to other undesirable side effects, some people are not able to take certain drugs. In addition, various other remedies are often proposed. For instance, medications and devices are available off-the-shelf. Some of these remedies are questionable in their treatment ability (meaning that there are no scientific empirical tests that demonstrate how well these products may work when compared against a placebo, nor what their effect may be in different motion environments). However, it has been observed by the inventors that devices such as wrist bands, either for applying pressure to suspected pressure points or applying an electric current to suspected pressure points, are not effective.

Research performed more than 20 years ago to investigate adaptation was conducted by having the subjects wear prism glasses that reversed vision in the horizontal plane (Jones and Mandl, 1981). It was discovered that when wearing these left-right reversing prisms many subjects would develop symptoms like those of motion sickness. Due to the variation in persons and motion environments, it was not clear if these symptoms would be replicable in actual motion environments. In one aspect of this testing, it was found that the symptoms were avoided if the visual surroundings were illuminated with a brief stroboscopic flash designed to provide a 3 µsec view of the visual scene. The flashes were kept brief to avoid any slip of an image on the retina, which is theorized to be related to motion sickness. It was also found that adaptation occurred during stroboscopic illumination, suggesting that mechanisms other than retinal slip may be involved in adapting to changes in the vestibular system. While the results were of interest, the use of stroboscopic flashes, except in the laboratory environment, does not provide a means for controlling motion sickness, even assuming the results are extended to motion environments.

Manufacturers presently sell LCD shutter glasses wherein the two lenses each operate independently, typically alternately, in order to produce a stereoscopic effect when viewing a computer screen. However, such LCD shutter glasses cannot be utilized to prevent motion sickness, and in some cases, have been found to cause discomfort especially when used for extended durations.

Various theories and devices intended for prevention of motion sickness are shown in the following patents.

U.S. Pat. No. 5,966,680, issued Oct. 12, 1999, to Hanan Butnaru, discloses a device and method which operates as an artificial labyrinth to eliminate sensory mismatch between the natural labyrinth/vestibular system and the vision system of an individual. The present invention provides an alternative means for the user to determine the true orientation of his body with respect to the surrounding environment. The method can be effected by means of a device which senses true body orientation and displays corresponding visual orientation cues that the brain can use to confirm other visual position information. The display can be projected into space in front of the user, directly onto the user's retina, or effected by pictorial scene averaging. The device is particularly useful in the rehabilitation treatment of persons suffering from vestibular nervous system defect or damage, and in providing relief to those suffering from the symptoms of nausea and/or vertigo which are often experienced as a result of the aforementioned sensory mismatch.

U.S. Pat. No. 5,067,941, issued Nov. 26, 1991, and U.S. Pat. No. 4,929,228, issued May 29, 1990, to Katherine A. Hendricks, disclose an anti-motion sickness apparatus which includes motion simulating means for providing a visually discernible wave motion image to create visually discernible orientation information for the user to confirm the inner ear information of the user, thereby preventing or at least greatly alleviating, the occurrence of motion sickness. A device helps position the motion simulating means in the field of view of the user. The method of use includes exposing the motion simulating means to the field of view of the user.

U.S. Pat. No. 5,829,446, issued Nov. 3, 1998, to John R. Tiffany, discloses a simulator which provides competing and opposing stimuli for objects appearing to approach or retreat from the user in order to reduce simulator sickness. A simulator controller monitors the pixels taken up by an object. When an object appears to take up more pixels, the controller interprets the object as appearing to approach the user. The controller inserts a complementary object which appears to do the opposite of the primary object detected by the simulator controller. Both objects are displayed on a video display viewed by the user.

U.S. Pat. No. 6,275,998 B1, issued Aug. 21, 2001, to David Tromble, discloses a vision occluding eye shield which completely blocks the peripheral vision of the wearer to the discernment of motion and which blocks most or all of the superior field of vision of the wearer, and preferably also blocks an upper portion of the inferior field of vision of the wearer, to the discernment of motion. When worn by a vehicle passenger the device prevents car sickness by blocking perception of objects passing through the peripheral field of vision in the side windows and through the front window, while allowing the wearer to focus on tasks or objects within the vehicle by looking through the unoccluded portion, or to look out the vehicle windows by slightly tilting the head back.

U.S. Pat. No. 5,647,835, issued Jul. 15, 1997, to Michael Martineau, discloses an apparatus and method for preventing motion sickness. The apparatus comprises a blinder attached to a support and positioned for confining the vision of a person susceptible to motion sickness to block all visual information indicative of motion.

U.S. Pat. No. 6,228,021, issued May 8, 2001, to Bruce Kania, discloses a method and apparatus used for relieving motion sickness, wherein a sensor senses a motion of an object and a sensory converter coupled to the sensor and converts the sensed motion to corresponding sensory signals for presentation to a user. The sensory signals include audio signals, display signals, white noise signals, pink noise signals, brown noise signals, and audio tone signals. The audio signals, white noise signals, pink noise signals, and brown noise sensory signals have a variation in spectral emphasis in proportion to the sensed motion, such as by varying a bandwidth, a center frequency, and an amplitude of a first range of the sensory signals. The display signals have a variation in a display characteristic and the audio tone signals have a variation in time intervals between successive audio tones. The audio tones may also include audio messages containing words. The sensory signals are used to resolve a conflict between vestibular, ocular, and proprioceptive inputs of the user, thus relieving motion sickness.

The above described prior art does not show the solution provided by the present invention. As taught by the present invention, it would be desirable to provide a relatively simple device that can be used without training. It would be desirable that the device be useable in every environment where motion sickness may be a factor including environments ranging from space flight to boating or cars. It would be desirable that this device results in very minimal or no side effects for practically everyone. It would be desirable that the device permit an operator to operate equipment including planes, boats, and/or a space station. It would be desirable that adaptation to the environment occur as the device is used.

Those skilled in the art have long sought and will appreciate the present invention that addresses these and other problems.

SUMMARY OF THE INVENTION

The device of the present invention can be used to prevent, and in some cases, cure motion sickness including balance problems and vestibular discomfort following surgical treatment. It is easily implemented and does not require training. In addition, the device will allow adaptation to specific motion environments allowing future exposure to that motion environment to be experienced without further intervention. Cost to the end user will be low. No such products are currently available.

Therefore, an object of the present invention is to provide an improved motion sickness prevention system, apparatus, and/or method for any motion environment including but not limited to cars, boats, planes, and spacecrafts.

Another object of the present invention is to provide a specific treatment for the motion sickness that occurs as a result of living and working in a microgravity environment (i.e., space flight).

One of many advantages of the present invention is that the system does not require training.

Another of the many advantages of the present invention is that a user may function within a motion environment while practicing the invention.

One of many features of a preferred embodiment of the present invention is a novel technique for preventing motion sickness.

Another of many features of a preferred embodiment of the present invention is eyewear such as glasses or goggles that may be utilized to prevent motion sickness.

These and other objects, features, and advantages of the present invention will become apparent from the drawings, the descriptions given herein, and the appended claims. It will be understood that above listed objects, features, and advantages of the invention are intended only as an aid in understanding aspects of the invention, are not intended to limit the invention in any way, and do not form a comprehensive list of such objects, features, and advantages.

Therefore, the present invention discloses a method to prevent motion sickness which may comprise one or more steps such as, for example only, providing eyewear with one or more shutter lenses that either simultaneously block vision to both eyes of a user through the one or more shutter lenses by closing the one or more shutter lenses or simultaneously permit vision to both eyes of a user through the one or more shutters lenses by opening the shutter lenses. Other steps may comprise opening and closing the one or more shutter lenses at an operating frequency. The opening of the one or more shutter lenses may be made for an exposure time. The exposure time may have a duration and the method may provide that the duration of the exposure time is less than a period of the operating frequency. In a preferred embodiment, the exposure time is less than about one half the period of the operating frequency.

The method may further comprise providing that the duration of the exposure time is short enough to prevent or substantially prevent retinal slip of an image through the one or more shutter lenses with respect to a sensing surface of a user's eye. In a preferred embodiment, the method comprises providing that the one or more shutter lenses comprise liquid crystal shutter lenses.

The method may further comprise providing the operating frequency is within a range less than about 50 Hz and/or varying the operating frequency in response to movement of a user's head. In one embodiment, the method may comprise providing at least one mode of operation wherein the operating frequency is fixed at an operating frequency less than about 15 Hz and may preferably be about 4 Hz.

In another embodiment, the method may comprise one or more steps such as, for instance, providing eyewear with one or more shutter lenses that either blocks vision through the one or more shutter lenses by closing the one or more shutters or permits vision through the one or more shutters by opening the shutter lenses, and/or opening and closing the one or more shutter lenses at an operating frequency less than about 50 Hz, and/or providing that an exposure time for each of the openings has a duration less than about one-half of a period of the operating frequency.

The method may further comprise providing that the duration of the exposure time for each opening is less than about one-fourth of a period of the operating frequency. In another embodiment, the method comprises providing a first mode of operation wherein the operating frequency is fixed at a frequency less than about 10 Hz and/or providing a second mode of operation wherein the operating frequency is variable and/or providing the operating frequency is variable in response to movement of the user's head.

In yet another possible embodiment the method may comprise one or more steps for operating eyewear comprising two liquid crystal lenses such as providing a sensor to measure at least one physical parameter and produce a signal, and/or opening or closing both of the two liquid crystal lenses simultaneously in response to the signal. The sensor may sense movement, such as movement of a user's head. The sensor may sense light such as, for example only, light that comprises a laser or other types of light.

An eyewear apparatus is disclosed for use in treating motion sickness, wherein the eyewear may comprise one or more elements such as, for example only, a frame adapted to be carried by a user, and/or one or more shutter lenses mounted within the frame, and/or a signal generator for producing a signal for opening and closing the one or more shutter lenses, and/or a controller for controlling an operating frequency of the signal generator. The controller may be selectively operable for operating the signal in a fixed operating frequency mode or a variable operating frequency mode. The operating frequency may remain substantially the same when treating motion sickness in the fixed operating frequency mode and the operating frequency may vary when treating motion sickness in the variable operating frequency mode.

In one embodiment, the signal generator further comprises a pulse generator and the pulse generator may be operable for producing pulses at the operating frequency. The pulses may have a pulse width duration less than about one-third and typically less than about one-half of a period of the operating frequency. The pulse width duration may vary and could, for instance, be about 10 milliseconds. However, the pulse width could be longer or shorter, and therefore the invention is not intended to be limited to this value or to other specific values. The eyewear may further comprise a sensor for measuring at least one physical phenomenon. The controller may be responsive to changes in the physical phenomenon for varying the operating frequency in the variable frequency operating mode. In one preferred embodiment, the sensor is responsive to physical movement of the user.

In another embodiment the eyewear may comprise one or more elements such as, for instance, a frame adapted to be carried by a user, two shutter lenses mounted within the frame such that the two shutter lenses cover the user's eyes, and/or a driver circuit operable for opening and closing the two shutter lenses simultaneously. The eyewear may comprise a sensor for producing a signal related to motion and/or changes in light.

The above and numerous other embodiments of the method and apparatus may be utilized in accord with the present invention.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

DESCRIPTION OF PREFERRED EMBODIMENTS

The present invention can be taken directly to the general population without modification of design principle and will treat most (if not all) forms of motion sickness.

Moreover, the present invention can be utilized in different phases of space flight, and will benefit all crew members without side effects.

Figure 1:
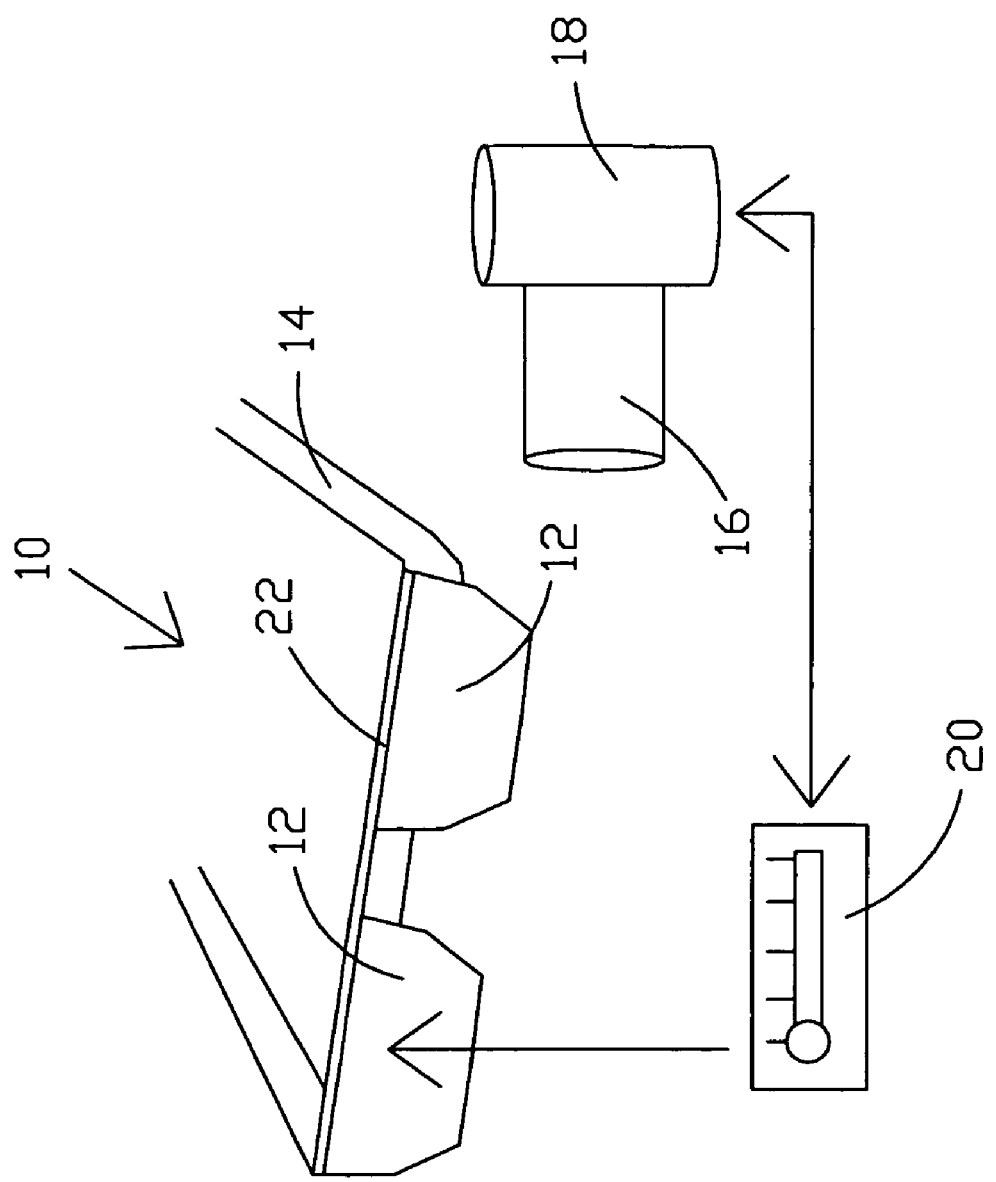
FIG. 1 is a perspective view of an apparatus in accord with the present invention that may be utilized for preventing motion sickness.

Referring now to the drawings and more specifically to FIG. 1, there is shown an embodiment of motion sickness countermeasure 10 in accord with the present invention that may be utilized to prevent motion sickness in either space or terrestrial environments.

Figure 2:
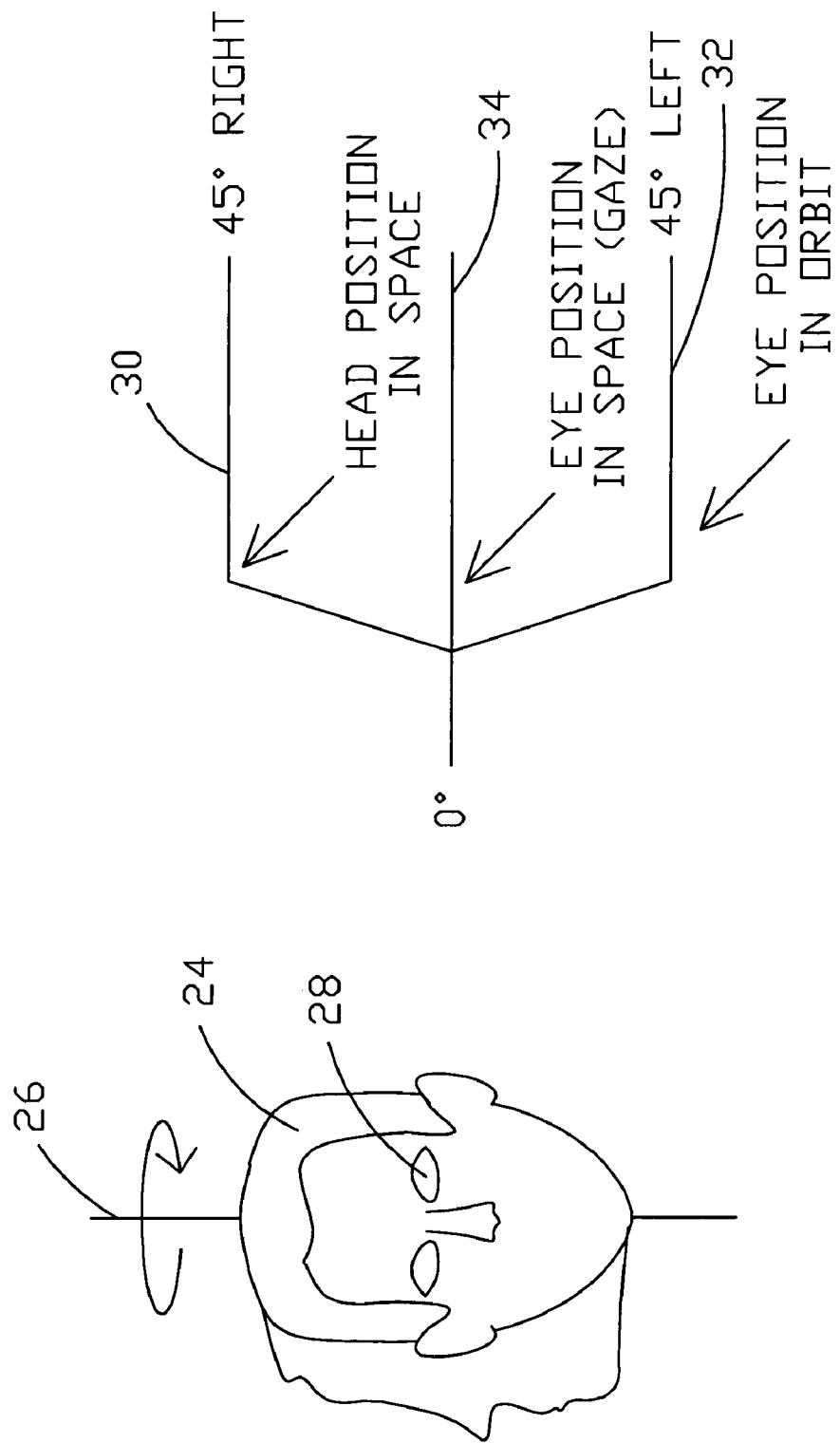
FIG. 2 is a schematic illustrating the concept of vestibular-ocular reflex whereby movements of the head in a motion environment should be offset by movements of the eyes to maintain a steady gaze to thereby avoid retinal slip and motion sickness.

Research on the control of sensory function, specifically, target acquisition and motor function that was completed as a part of the Extended Duration Orbiter Medical Program (EDOMP) and the long duration Shuttle-Mir and NASA-Mir programs has suggested that difficulties with motion sickness and motor control may have a common root in retinal slip. The vestibular system normally coordinates head movement and eye movement so that the relative head and eye movements effectively cancel out to permit a person to keep his or her eyes affixed on a target in a motion environment. What may be referred to as gain changes in the vestibular system as a function of space flight result in modification of eye movements and subsequent control of the major postural muscles. FIG. 2, also discussed hereinafter, illustrates the concept of occularmotor gain changes vestibular system. These changes in gain produce movement of the eyes that cause images to either race across the retina (gains greater than unity) or move only part way across the retina (gains less than one). Gains either greater or less than unity produce adaptive responses that compromise vision, postural stability and fine motor control. A further consequence of changes in occularmotor gain during the adaptation process is motion sickness.

The present invention presents visual/vestibular information to the central nervous system in a way that prevents retinal slip, which is believed to be a primary factor in the development of motion sickness symptoms. A preferred embodiment of the present invention utilizes two fast acting, low voltage liquid crystal shutter lenses 12 within eyewear such as frames, glasses, or goggles 14. However, any suitably fast acting shutters, including mechanical shutters or other types of shutters, could conceivably be utilized in a headset to practice the invention. Moreover, a single liquid crystal shutter lens could be utilized. If desired, the single liquid crystal shutter lens could be made wide enough to permit vision through both eyes. Thus, the present invention preferably comprises at least one liquid crystal shutter lens, and typically two simultaneously opening/closing liquid crystal shutter lenses, that preferably permit both eyes to simultaneously view the same scene or view or visual information. However, it is also conceivable that the operating ranges of frequency and exposure times, as discussed hereinafter, for the two lenses may be different. Thus, alternately or otherwise controlling opening and closing of two different shutter lenses 12 at the operating frequency ranges and/or exposure durations discussed herein may also be utilized to treat motion sickness. Moreover, shutter lenses 12 and frames, goggles, or glasses 14 shown in FIG. 1 may be of many different shapes and styles, as desired.

One preferred embodiment of motion sickness countermeasure 10 utilizes additional sensors/controls. For example, when coupled with measurement of head movement from x rate sensor 16 and y rate sensor 18, and/or other sensors to provide displacement/velocity information, images seen through shutter lenses 12 can be presented to the brain in such a way that neither vision nor visual performance is compromised. In a preferred embodiment both lenses 12 operate simultaneously and in an identical manner with identical timing. Motion sickness countermeasure 10 is preferably worn on the head and can be used by practically anyone. (However, see the discussion hereinafter concerning the relatively small number of persons who may be advised not to use products of this type except under the advice of their physician.) Motion sickness countermeasure 10 can be used without training and in every environment where motion sickness may be a factor. Because no drugs are involved, there are virtually no side effects. Motion sickness countermeasure 10 will function in environments ranging from space flight to boating or cars.

Software may be utilized to accept signals from sensors designed to measure head velocity, such as rate sensors 16 and 18. Control unit 20 may be utilized to control lenses 12 for the control of motion sickness. Thus, control unit 20 may effectively be a small onboard computer. Control unit 20 can be provided in a very small package and could be mounted to frame, goggles, or glasses 14. It will also be understood that control unit 20 can be simplified in hardware form, and may simply comprise oscillator and liquid crystal driver circuits. Moreover, for highly simplified and low cost embodiments of the invention, it may be desirable not to utilize rate sensors 16 and 18. Glasses or goggles 14 can be built to operate independently from one or more separate components such as the rate sensors and even control unit 20. In addition, the use of the software, rate sensors and a computer can be utilized to enhance the performance of the device.

While a number of different environmental factors can induce motion sickness, a common factor associated with every known motion environment is the concept of sensory confusion or sensory mismatch. Motion sickness is believed to be the product of misinformation arriving at a central point, called the neural integrator, in the central nervous system. When information from the ears, joints and pressure receptors, and the visual system are all in agreement as to our orientation there is no motion sickness. However, when one or more sensory inputs to the brain is not expected, or is in conflict with what is anticipated, the end product is motion sickness. Thus, it is possible to have motion sickness symptoms when the individual is at rest but the visual environment is in motion (optokinetic).

In almost every known environment that induces motion sickness, there is retinal slip (images that are normally held stationary on the sensory surface of the eye move) that is caused by a change of gain (adjustment) of the vestibular system. An intact vestibular system is necessary for motion sickness to occur. A product of the change in vestibular gain is eye movements that do not match what is expected in the central location in the brain. Prevention of retinal slip, and hence the prevention of sensory mismatch, will reduce the possibility for motion sickness to occur. FIG. 2 depicts the Vestibular-Ocular Reflex or VOR. As head 24 rotates around axis 26 with eye 28 is fixed on a target, then eye 28 rotates equally and oppositely in the head, assuming the gain of the vestibular system is unity. The associated graph of movement in FIG. 2 provides an example of unity gain during a coordinated head and eye movement. Movement of head position as indicated at 30 matches the movement of eye position as indicated at 32 to provide that the eye position in space is effectively the same as indicated at 34. In the example of FIG. 2, the gain of the vestibular system is one because the combined movements are effectively cancelled out with respect to movement of the image on the retinal surface. This reflexive action ensures that the target will remain fixed on the retinal surface, and that the target will not blur.

Gain changes in the VOR may occur as a function of space flight or other motion environments. Other factors, such as aging, disease, and medications, can also modify the gain of the vestibular system. In one experiment, data obtained from four subjects on a Spacelab flight were obtained by a voluntary head shake at two different frequencies (0.33 and 1.0 Hz) under two different conditions (with vision while looking directly at a fixation spot approximately 1.0 m in front of the subject, and during complete darkness where the subject tried to imagine the fixation spot). It was found that, gain is lower during the flight and immediately post flight. One possible explanation for the reduction in gain relies on a change in the adaptive neural strategy wherein gain is reduced to keep the target image from racing across the surface of the retina. That is, it may be more efficient to reduce the apparent velocity of the image and at least maintain the image on the same quadrant of the retina.

When making preliminary measurements of eccentric gaze-holding in the few astronauts and cosmonauts available to us, it was also observed that in addition to changes in the central neural integrator's ability to maintain eccentric gaze, what appeared to be square-wave jerks (SWJs) in eye movement. There is a close association of the neural substrate that both supports SWJs and mediates gaze-holding. In situations where adaptive changes are required (in this case the modification of gaze parameters by changing inertial environments), those mechanisms used to mask an imbalance or pathology may show decompensation.

It typically requires several days of recovery after a space flight before oscollopisa (visual blurring) or vestibular gain returns to normal, and the subjects are capable of reading the characters at approximately 100% (data acquired from J. Bloomberg). One subject had a high rate of SWJs. It is interesting to note that when this subject performed this test within 24 hr after landing, there were no errors. That is, the subject performed at preflight levels. We believe that a post flight decrement did not occur because the subject, via the SWJs, was effectively strobing the environment (although there are several other feasible arguments for the better than average performance). In addition to the lack of gain changes in the vertical plane during the dynamic visual acuity test, this subject did not present with strong post flight motion sickness symptoms. Each SWJ may act to effectively "freeze" the visual scene. Motion sickness countermeasure 10 provides the "freezing" function automatically for all persons.

Thus, motion sickness countermeasure 10 works to prevent motion sickness (in all types of motion environments) by limiting retinal slip. The innovation does this by limiting input to the eyes that are brief snapshots of the visual environment. The snapshots are brief enough that each snapshot freezes the image on the retina. Motion sickness countermeasure 10 does this by using liquid crystal shutter lenses 12 as electronic shutters mounted in what may simply and conveniently be a regular pair of glasses, such as frames, glasses, or goggles 14. In one presently preferred embodiment, the nominal rate of strobing of the snapshots is kept low, about 3 or about 4 Hz.

Exposure time (i.e., the amount of time electronic shutters is clear) is kept short. In one presently preferred embodiment, visual exposure is provided for each snapshot about ⅓ of the period of the operational frequency. In the event that a higher rate of strobing is necessary to accommodate very fast head movements, the rate of strobing, but preferably not strobe duration, can be controlled in response to data from angular rate sensors 16 and 18, which may attached to the frame of the glasses 14. The rate of strobing may also be manually controlled, if desired. In one presently preferred embodiment, exposure time is preferably fixed but the exposure time could also be variable, selectable, and/or controllable, as desired. The exposure time is preferably set short enough to prevent retinal slippage.

In a preferred embodiment, fast response PDLC material is utilized in lenses 12 whose state from dark to clear can be altered via abrupt changes in voltage potentials and/or changes in electric current. Preferably, frames, goggles, or glasses 14 comprise custom made eye glass frame member 22 in which the PDLC lenses are installed. Lenses 12 and eye glass frame member 22 may be shaped to provide that the sensory stimulation of interest that reaches the eyes passes through lenses 12.

While FIG. 1 shows provides one possible conceptual drawing/diagram of motion sickness countermeasure 10, many possible embodiments and designs may be utilized. In one preferred embodiment, rate sensors 16 and 18 to measure head velocity measure movement around at least two axes such as the y-axis (yaw) and the x-axis (pitch) planes. However if desired, and perhaps depending on the motion environment, the z-axis (roll) may also be sensed in conjunction with or in place of one or more of the other rate sensors.

Figure 3:
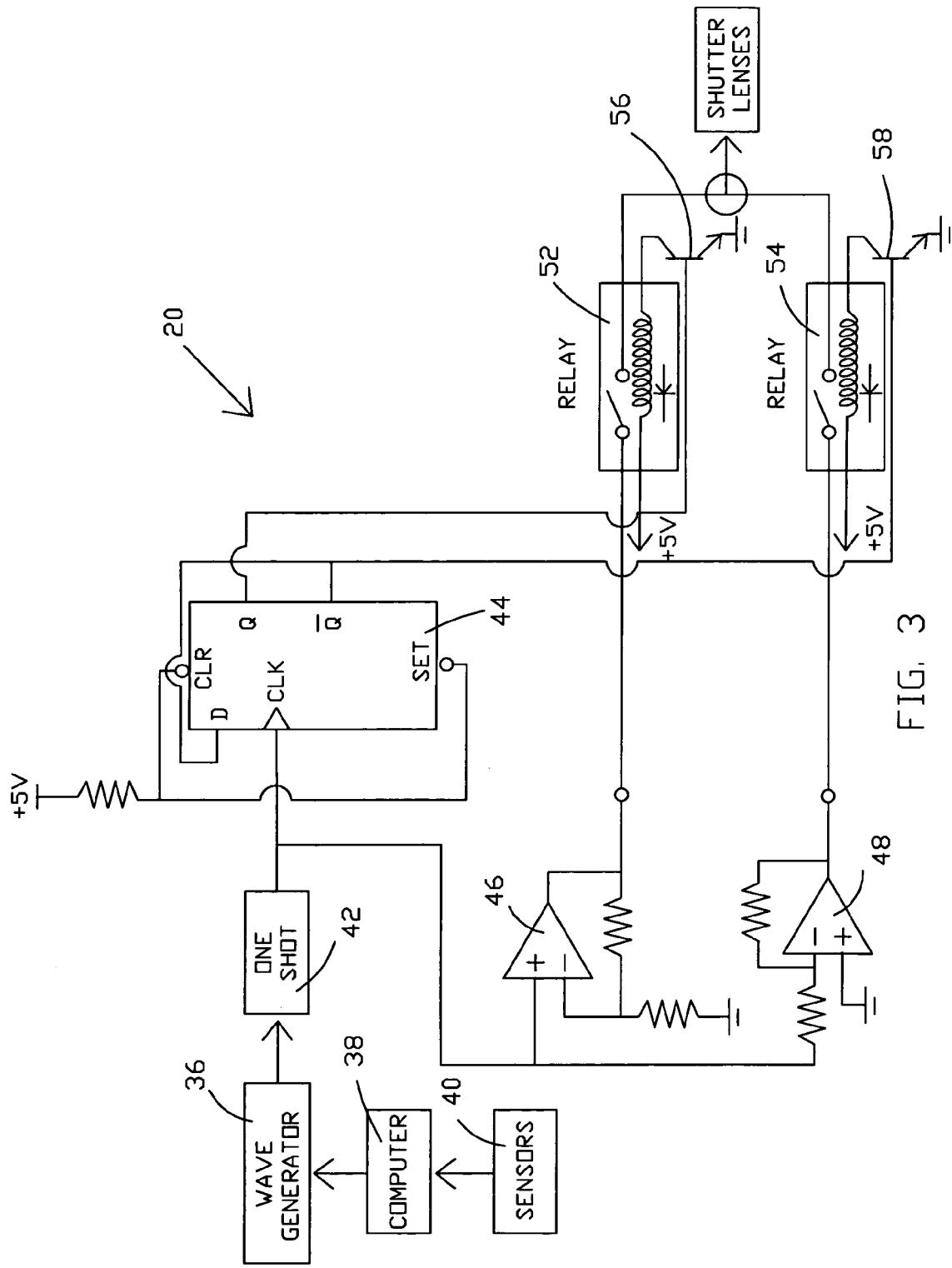
FIG. 3 is an electronic schematic that illustrates the concepts of operation of liquid crystal shutter lenses in accord with the present invention.

Controller unit 20 may be comprised of a low frequency oscillator and a switchable driver coupled to both rate sensors. Some details of one possible embodiment for controller 20 are shown in FIG. 3. Many other embodiments could also be constructed. Square wave generator 36 integrated circuit may be used as an inexpensive oscillator although any suitable oscillator circuit and/or signal generator circuit could be utilized. As one possible example of another embodiment, a processor or software controlled computer or controller device could be utilized to replace square wave generator 36, one-shot 42, and D-flip flop 44.

The frequency of operation of square wave generator 36 may be fixed or variable, or selectively fixed or variable, depending on the embodiment. If fixed, the frequency may preferably be about 4 Hz but preferably within the range from about 2 Hz to about 6 Hz or preferably at least in the range from about 0.5 Hz to about 10 Hz. At a frequency of about 4 Hz, many slow activity functions can be performed such as being an observer in a boat or perhaps even operating a boat under many circumstances. If the frequency is variable, a manual or automatic frequency control may be provided. If manual, then the control may be switchable or continuously variable. As activity becomes faster, then the frequency of operation may be increased. For instance, frequencies from about 25 Hz to about 50 Hz may be utilized to accommodate a user in a quick motion or faster activity operation, e.g., an abrupt or quick movement of the head, although a preferred upper limit of frequency may be about 40 Hz. If the frequency control is automatic or selectively automatic, then a computer or other processing means 38 may be utilized to process motion sensor information such as data from sensors 40, such as rate sensors. As motion of the head increases, then software for processing means 38 will cause an increase in frequency which is a function of the type of motion.

In this embodiment, the signal from oscillator 36 is fed to one-shot 42. One-shot 42 produces a pulse with a pulse width that controls the exposure timing, i.e., the time shutter lens 12 is open. This exposure timing may be set at a desired duration that effectively prevents retinal slip. In one preferred embodiment the duration is 5 milliseconds. In any event, the exposure timing will preferably be significantly shorter than the period of operation of the oscillator. As another example, at 40 Hz for example, the period of the oscillation is 25 milliseconds. Thus, in one preferred embodiment, the exposure timing is less than one-half the period of oscillation but could be smaller as desired, e.g. in another embodiment the exposure timing may be at least four to five times shorter than the period of oscillation frequency. The exposure timing should be in the range of values whereby the image is exposed to the retina long enough to sense the image but quickly enough so that the image does not move an appreciable amount over the retina. If suitable shutter lenses were available, the exposure time may be in the microseconds but physical limitations of shutter lenses presently require an exposure time in the millisecond range. The output of one-shot 42 is normally at a high level, e.g., about 5 volts, with negative going pulses, e.g., 0 volts, produced at the frequency of oscillator 36 with a pulse width of a desired duration suitable for preventing retinal slip.

The output of one-shot 42 is fed to the liquid crystal device (LCD) driver circuitry for this embodiment and is therefore related to the specifications of the LCD. For this example, the LCD specifications for maximum durability require that positive and negative signals applied to the LCD cancel out over the operating cycle of the LCD. Because manufacturing processes may change over time, and for different types of liquid crystal material that may be utilized, it is anticipated that the liquid crystal driver circuitry may change accordingly. Moreover, other circuitry might be utilized to perform the same driver functions.

However, in order to provide signals that correspond to the specifications of the LCD, the output of one shot 42 is separated into two paths leading to op amps 46 and 48. Op amps 46 and 48 produce inverted signals, or pulses, with respect to each other at desired specification voltages. The pulses have a pulse duration, in one preferred embodiment of 5 milliseconds during which time the lenses 12 are opened to permit viewing therethrough. The pulses are applied to both lenses 12. However, the pulses from each op amp are applied alternately at different times by means of switching circuitry controlled by D flip-flop 44. Thus, only one pulse from one op amp drives both lenses 12 at a time. To accomplish this, D flip-flop alternately activates relays 52 and 54 so that the pulses produced by op amps 46 and 48 are applied to lenses 12 alternately, i.e., the pulses produced by op amps 46 and 48 are not applied simultaneously. Transistors 56 and 58 are utilized to increase the speed of operation of relays 52 and 54. The switching circuitry could also comprise other types of gates and/or other timing arrangements such as where the gates have a delayed timing with respect to the pulses whereby the switching speed of the relays is less important. The alternately, relatively inverted pulses applied to liquid crystal shutter lenses 12 average out to zero in accord with the specifications of the particular shutter lenses 12 utilized. In this particular type of liquid crystal device, each lens 12 may comprise two stacked liquid crystals wherein light passes if both liquid crystals are polarized in the same direction and light is blocked if both liquid crystals are polarized in different directions. The pulses alternately change the polarization of one or more of the liquid crystals. It will be understood that other types of driver circuits can be utilized in accord with the present invention for other types of liquid crystal lenses.

In operation, the use of glasses/goggles 14 for the prevention of motion sickness is quite simple. As explained above, the glasses/goggles preferably function by opening for brief moments at a desired rate (from about 4 Hz to about 40 Hz) to permit the user to view the visual environment while simultaneously preventing image slip on the retina.

In one preferred embodiment, glasses/goggles or head set 12 has four basic modes of operation as discussed subsequently. However, as explained earlier, there are many possible variations of operation.

In mode 1, the user simply selects either the On or Off setting for control unit 20. In mode 1, the user can manually select the frequency of operation.

Mode 2 is a static mode that clears the PDLC (polymer dispersed liquid crystal), LCD, or any other type of liquid crystal lens material making it possible to see through the lens material. It is possible to combine modes 1 and 2 if desired via control unit 20.

In mode 3, the wearer can select the standard frequency of about 4 Hz, i.e., the PDLC material is turned on and off four times in one second. Under most conditions of operation, this lower operation frequency rate is preferred for uses that are relatively passive, e.g., passengers in moving vehicles, boats, etc.

In mode 4, the operation frequency of the glasses/goggles may be under the control of rate sensors 16 and 18 (or other transducers capable of sensing velocity/acceleration of the head). The rate sensors (or other transducer) send voltage controlled data to the control unit 20. That information is converted to frequency information that will drive the PDLC material to change state (clear to dark, and then back to clear again) at frequencies preferably up to about 40 Hz. This mode of operation produces a type stroboscopic effect that will "freeze" images on the retina even while head movements are made in either the horizontal or vertical planes. When operating in mode 4, the glasses or goggles can be worn by individuals that are actively engaged in activity and/or movement.

While glasses/goggles/headset 14 are preferably utilized for preventing, treating, and/or adapting to motion sickness, they may have other applications. The capture of images will be useful for DoD (Department of Defense) applications where humans are exposed to environments where vibration is a problem. For example, the glasses/goggles might be utilized in high performance aircraft, both fixed wing and helicopters when it is necessary to read instrument displays that can become blurred by vibration or vestibular-ocular responses. In this example, then the circuit of FIG. 3 could be modified so that sensor 40 is a vibration sensor and the software may be designed to open shutter lenses 12 at selected times which would help keep the instrument readings constant. Computer 38 may then drive one shot 42 directly.

Glasses/goggles 14 could be used as sunglasses and/or as a protection against bright light (everything from sunbathing to atomic flashes). There is apparently some concern within the DoD that high-powered lasers can be fired from the ground in an attempt to temporarily blind a pilot. With proper modifications such as a laser sensor and suitable trigger circuit, glasses/goggles 14 proposed in this disclosure could be used to shutter the pilot's vision when a laser is on target. In this case, the pulse width may be widened to correspond to the time the laser is on target so that shutter lenses 12 remain closed so long as the laser is on target and while the pilot's head is facing the laser. Thus, different types of sensors may be utilized simultaneously.

It is also feasible to use glasses/goggles 14 to treat a variety of neuro-vestibular problems, ranging from balance disorders to postoperative recovery from head trauma or $8^{th}$ cranial nerve damage (including surgical intervention).

For the most part, the components required to develop, build and manufacture glasses/goggles 14 for this innovation are primarily off-the-shelf parts that can be assembled to meet the requirements described above for protection against motion sickness.

Glasses/goggles 14 are low maintenance hardware, and if packaged as a unit should require nothing more than cleaning (just as you would any eye glasses). Because there are no moving parts it is expected that the glasses/goggles will remain reliable in all environments given reasonable care.

Safety of the glasses/goggles requires that their use be limited to those individuals who are not sensitive to epileptic seizures. Photosensitive epilepsy is the name given to that form of epilepsy in which seizures are provoked by flickering light that is encountered in everyday life. Photosensitive epilepsy is rather rare. About one person in every 200 is diagnosed as having epilepsy. Out of these only one person in every 10,000 has photosensitive epilepsy. The age of onset for photosensitive epilepsy is usually between 9 and 15 years. Girls are more sensitive than boys. It is rare to have onset sensitivity before the age of 5 or after the age of 20. Most individuals are aware that they suffer from this type of epilepsy and therefore, it is relatively easy to screen for those that have photosensitive epilepsy. Triggers for photosensitive epilepsy include: (1) viewing a television screen (most common), playing a video game, or computer graphics; (2) a light source that flickers at a low frequency; (3) sunlight coming through a line of trees; (4) sunlight on water; (5) looking out a train window; (6) stroboscopic lights; and (7) looking at a moving escalator. Even these triggers are not all positive for induction of photosensitive epilepsy, and require a number of other factors: (1) frequency of the light stimulation; (2) light intensity; (3) background illumination; and (4) wavelength of the light. And usually, people with photosensitive epilepsy have had seizures both with and without flashing (flickering) light. While sensitivity varies as a function of flash frequency, it has been determined that 96% of people with photosensitive epilepsy are sensitive to light flashes from about 15 to about 20 Hz.

To reduce the possibility that motion sickness countermeasure 10 will induce photosensitive epilepsy in susceptible individuals, the basic flash rate of the glasses/goggles is preferably less than about 4 Hz (a frequency where there is little or no likelihood of inducing an epileptic episode, and taken with adherence to the following screening criteria should preclude any safety issues). Thus, those persons with this disability may use motion sickness countermeasure 10 in mode 3, or in an embodiment which only operates as per mode 3, which is the basic 4 Hz estimated rate. Advice of a physician should also be obtained for those persons.

Additional warnings would suggest that motion sickness countermeasure 10 should not be used by any individuals who have been diagnosed with any form of epilepsy unless under the care of a physician. Other persons who should obtain advice from a physician before use are persons' in whose family there is a history of epilepsy. Additionally, anyone who has ever had an adverse reaction of any kind to stroboscopic illumination, anyone who has ever had a neurological seizure of any kind, anyone who has ever displayed or experienced episodes of blank staring, twitching of the mouth or face, jerking movements in other parts of the body, the inability to talk or respond, or sensory hallucinations, and anyone taking any of the medications, or has ever taken any medications that are used to treat epilepsy should not use motion sickness countermeasure 10 unless under the supervision of their physician. These drugs include Carbamazepine (Tegretol, Tegretol-XR, Carbatol), Ethosuximide (Zarontin), Gabapentin (Neurontin), Lamotrigine (Lamictal) Phenobarbital, Phenytoin (Dilantin), Tiagbine (Gabitril), Topiramate (Topamax), Valproate (Depakote), and Sodium Valproate (Valproic Acid).

Figure 4:
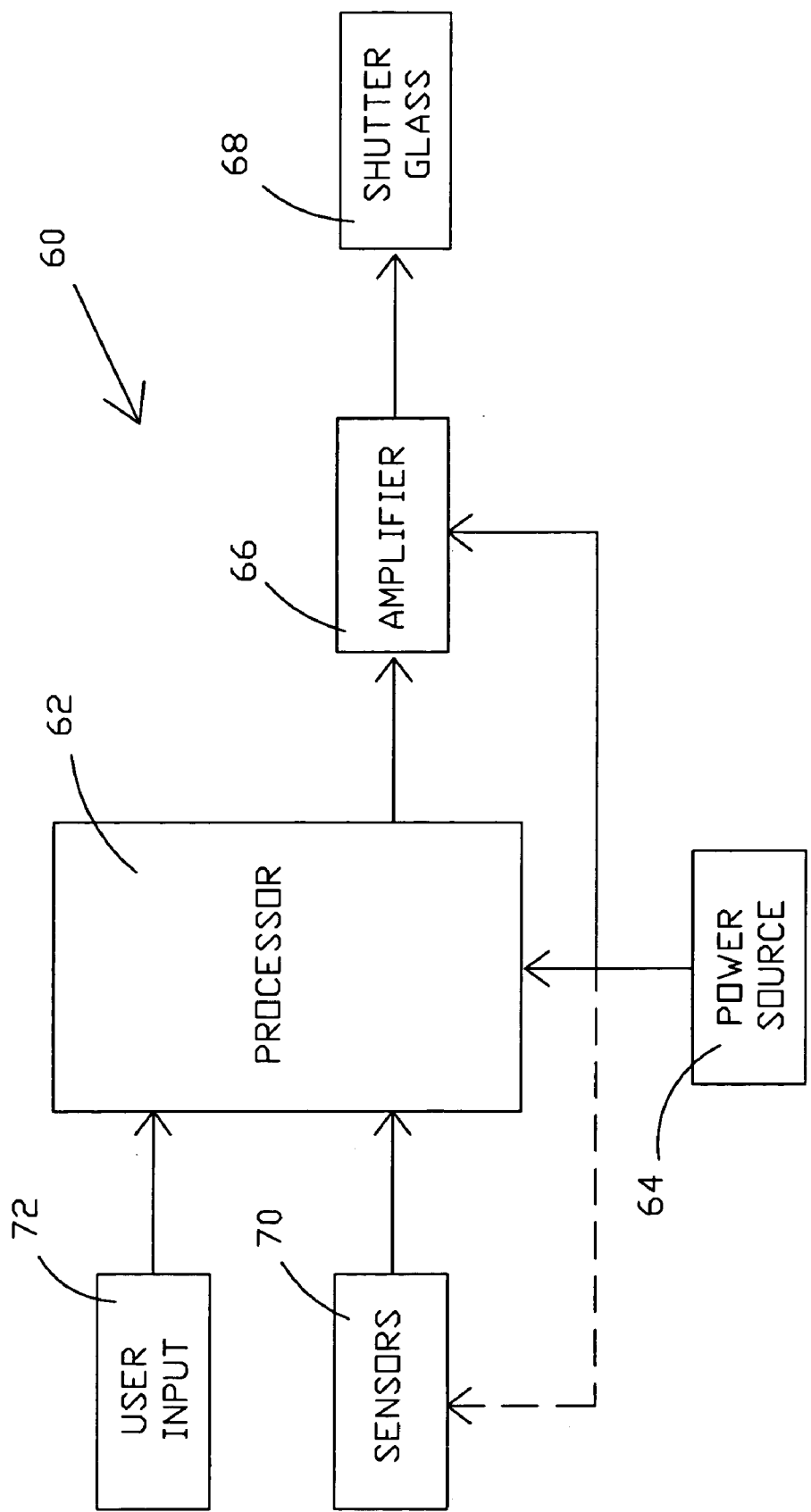
FIG. 4 is a block diagram schematic of another embodiment of a shutter lens eyewear apparatus in accord with the present invention.

FIG. 4 shows another embodiment of the present invention using control system 60 for controlling any type of shutter glasses 68 including any liquid crystal shutter glasses or any other types of shutter glasses. Processor 62 which may be a microprocessor, computer, programmable component, or other circuitry is utilized to produce the desired control waveforms (voltages and/or currents) necessary to control shutter glasses 68 as per the specifications of the particular type of shutter glasses utilized. Amplifier or driver 66 may be used as necessary to buffer, electrically isolate, amplify, and/or for other purposes needed to thereby drive shutter glasses 68 to open and close at the desired operating frequencies and exposure durations as discussed herein. Power source 64 to operate control system 60 may be any suitable type including batteries, power line adaptors, car voltage, airplane power supplies, or the like which may vary depending on the type of power available. User input 72 may include any desired controls to operate system 60 such as switches, knobs, voice control, LED, remote controls, transmitters, panels, keys, or the like as desired. Sensors 70 may or may not be utilized depending on the particular implementation. For instance, control system 60 may simply operate at a fixed or desired frequency without sensors. In one preferred embodiment, motion sensors as discussed herein may be utilized to control the operating frequency. However, other types of sensors may also be utilized as discussed herein. Control system 60 may be implemented as one or more integrated circuits and/or with discrete components. While control system 60 is representative of one embodiment of the invention, the present invention may be implemented with any type of circuit that can be utilized to drive shutter glasses 68 in the desired manner discussed herein to treat motion sickness.

Thus, the present invention pertains to an apparatus and method for preventing motion sickness associated with both space travel and terrestrial motion environments. The primary function of the motion sickness countermeasure 10 is to prevent retinal slip. Retinal slip occurs when there is a gain change in the vestibular-ocular system. Gain change is usually encountered when an individual is exposed to a motion environment. When the head is moved, and the vestibular-ocular gain is unity (i.e., input is equal to output) the eyes will move equally and directly opposite the head movement. This allows us to see clearly without visual blurring. When the gain is not equal to one, they eye does not move exactly equally and opposite the head. The end result is slippage of the image on the retina of the eye. This disparity frequently causes individuals to become motion sick. It may also make them unsteady, dizzy, and prone to falls.

Motion sickness countermeasure 10 prevents all of these conditions. To overcome retinal slip the individual wears a pair of glasses/goggles 14 that have electronic shutters or lenses 12. The shutter speed (i.e., number of times it opens/closes in one second) can be controlled by the wearer, or set so that the shutter speed is servo controlled by the velocity of the users head movements. In this latter mode, shutter speed is variable and will allow for significantly more "snapshots" of the visual surround. However, typical shutter speed will default to the 3 or 4 Hz estimated frequency range. Exposure time (i.e., amount of time the shutter is open) is kept short, typically from about ½ to about ¼ of the period of the operational frequency. However, the exposure time may be much shorter. For instance, with good lighting, the shutter speed could theoretically be in the range of microseconds. However, the maximum LCD shutter speed may not permit such a fast shutter speed. Overall the shutter speed is selected to provide optimal amount of information about the external environment, and the exposure time is kept short to prevent the image of the external environment from moving on the retina while the shutter is open. For instance, the arc of movement of the visual image over the sensing surface of the eye may be less than a few arc degrees to effectively eliminate retinal slip. Thus, for purposes herein movement of the visual image less than about a few degrees, e.g., five arc degrees over the sensing surface is considered to eliminate retinal slip with less movement being better. Many kinds of motion environments, such as a rolling motion environment on a boat, are relatively slow speed movements so that the image may move less than one arc degree over the sensing surface with a shutter speed of about 50 milliseconds.

An interesting augmentation to the original purpose of this device is that contrary to existing theory (where retinal slip is required for a modification of behavior), subjects in our clinical trials seem to be learning (i.e., adapting to the provocative environment) while wearing glasses/goggles 14. Therefore, glasses/goggles 14 not only protect against motion sickness symptoms and associated vestibular side effects, but they may also be useful as temporary protection in specific motion environments while allowing rapid learning. This means, in effect, that when learning has occurred, use of glasses/goggles 14 will no longer be necessary in that specific environment (e.g., boating sailing, car sickness, etc.) because the subjects/patients will have adapted to that environment.

In general, it will be understood that the drawings are intended to describe the concepts of the invention so that the presently preferred embodiments of the invention will be plainly disclosed to one of skill in the art but are not intended to be manufacturing level drawings or renditions of final products and may include simplified conceptual views as desired for easier and quicker understanding or explanation of the invention. As well, the relative size/type/arrangement of the components may be greatly different from that shown and still be in accord with the spirit of the invention. The processing software and/or hardware may be quite different than the disclosed presently preferred embodiments and still operate very much in accord with the invention as disclosed hereinbefore and as claimed hereinafter.

The term "about" as used herein may be applied to modify any quantitative representation that could permissively vary without resulting in a change in the basic function to which it is related. For example, the basic flash rate of the glasses/goggles as disclosed herein my permissively be greater than 4 Hz within the scope of the invention if there is little or no likelihood of inducing an epileptic episode and taken with adherence to previously described screening criteria.

Therefore, the foregoing disclosure and description of the invention are illustrative and explanatory thereof and various changes in the method steps and also the details of the apparatus may be made within the scope of the appended claims without departing from the spirit of the invention.

What is claimed is:

1. A method to prevent motion sickness, comprising:
   providing eyewear with one or more shutter lenses, said one or more shutter lenses being operable for simultaneously blocking vision to both eyes of a user through said one or more shutter lenses by closing said one or more shutter lenses, said one or more shutter lenses being operable for simultaneously permitting vision to both eyes of a user through said one or more shutter lenses by opening said one or more shutter lenses;
   opening and closing said one or more shutter lenses at an operating frequency, each said opening of said one or more shutter lenses being made for an exposure time, said exposure time having a duration; and
   providing that said duration of said exposure time is less than a period of said operating frequency.

2. The method of claim 1, further comprising:
   providing that said duration of said exposure time is short enough to prevent retinal slip of an image through said one or more shutter lenses with respect to a sensing surface of a user's eye.

3. The method of claim 1, further comprising:
   providing that said one or more shutter lenses comprise liquid crystal shutter lenses.

4. The method of claim 1, further comprising:
   providing said operating frequency is variable within a range less than about 50 Hz.

5. The method of claim 4, further comprising:
   varying said operating frequency in response to movement of a user's head.

6. The method of claim 4, further comprising:
   providing at least one mode of operation wherein said operating frequency is fixed at an operating frequency less than about 10 Hz.

7. A method to prevent motion sickness, comprising:
   providing eyewear with one or more shutter lenses that either block vision through said one or more shutter lenses by closing said one or more shutter lenses or permit vision through said one or more shutter lenses by opening said one or more shutter lenses;
   opening and closing said one or more shutter lenses at an operating frequency less than about 50 Hz; and
   providing that an exposure time for each said opening has a duration less than about one-half of a period of said operating frequency.

8. The method of claim 7, further comprising:
   providing that said duration of said exposure time for each said opening is less than about one-fourth of a period of said operating frequency.

9. The method of claim 7, further comprising:
   providing a first mode of operation wherein said operating frequency is fixed at a frequency less than about 10 Hz.

10. The method of claim 7, further comprising:
    providing a second mode of operation wherein said operating frequency is variable.

11. The method of claim 10, wherein said operating frequency is variable in response to movement of the user's head.

12. A method to prevent motion sickness, comprising:
    providing eyewear with one or more shutter lenses that either block vision through said one or more shutter lenses by closing said one or more shutter lenses or permit vision through said one or more shutter lenses by opening said one or more shutter lenses;
    opening and closing said one or more shutter lenses at an operating frequency; and
    providing at least one mode of operation wherein said operating frequency is fixed at a frequency less than about 15 Hz.

13. The method of claim 12, further comprising:
    providing a second mode of operation wherein said operating frequency is variable.

14. The method of claim 12, wherein said operating frequency is variable in response to movement of the user's head.

15. The method of claim 12, further comprising:
    providing that an exposure time for each said opening has a duration less than about one-half of a period of said operating frequency.

16. The method of claim 15, wherein said exposure time is less than about 10 milliseconds.

17. A method of operating eyewear for the treatment of motion sickness, said eyewear comprising two liquid crystal lenses and carried by a user, said method comprising:
    providing one or more sensors to measure at least movement of said user's head and produce a signal; and
    selectively opening or closing both of said two liquid crystal lenses simultaneously responsively to said signal.

18. The method of claim 17, wherein said one or more sensors comprises two or more sensors to further sense light.

19. The method of claim 18, wherein said light comprises a laser.

20. The method of claim 17, further comprising:
    opening and closing both of said liquid crystal lenses at an operating frequency, each said opening of said liquid crystal lenses being made for an exposure time, said exposure time having a duration; and
    providing that said duration of said exposure time is less than a period of said operating frequency.

21. A method for treating or preventing motion sickness wherein a subject experiences movement as a result of said motion environment, said method comprising:
    said subject wearing shutter lenses in said motion environment;
    operating said shutter lenses to thereby control retinal slip of said subject while said subject views said motion environment through said shutter lenses.

22. The method of claim 21, further comprising opening and closing said shutter lenses at an operating frequency.

23. The method of claim 22, wherein said operating frequency is a fixed frequency.

24. The method of claim 22, wherein said operating frequency is a variable frequency which varies in response to said movement.

25. The method of claim 22, wherein said opening of said shutter lenses is for an exposure time.

26. The method of claim 25, wherein said exposure time is less than one-half of a period of said operating frequency.

27. A method for adapting a subject to a motion environment wherein said subject experiences movement as a result of said motion environment, said method comprising:
wearing shutter lenses in said motion environment;
opening and closing said shutter lenses at an operating frequency; and
removing said shutter lenses after said subject has adapted to said motion environment.

28. The method of claim 27, further comprising selectively providing that said operating frequency is fixed or variable.

29. The method of claim 27, further comprising opening said shutter lenses for an exposure time having a duration less than one-half of a period of said operating frequency.

30. Eyewear for use in treating motion sickness, said eyewear comprising:
a frame adapted to be carried by a user;
one or more shutter lenses mounted within said frame;
a means for producing a signal for opening and closing said one or more shutter lenses; and
a means for controlling an operating frequency from greater than 0 Hz to about 15 Hz of said means for producing, said means for controlling being selectively operable for operating said signal in a fixed operating frequency mode or a variable operating frequency mode, said fixed operating frequency remaining substantially the same when treating for said motion sickness in said fixed operating frequency mode, said variable operating frequency varying when treating for said motion sickness in said variable operating frequency mode.

31. The eyewear of claim 30, further comprising a means for measuring at least one physical phenomena, said means for controlling being responsive to changes in said physical phenomenon for varying said operating frequency in said variable frequency operating mode.

32. Eyewear for use in treating motion sickness, said eyewear comprising:
a frame adapted to be carried by a user;
one or more shutter lenses mounted within said frame;
a means for producing a signal for opening and closing said one or more shutter lenses;
a means for controlling an operating frequency of said means for producing, said means for controlling being selectively operable for operating said signal in a fixed operating frequency mode or a variable operating frequency mode, said operating frequency remaining substantially the same when treating for said motion sickness in said fixed operating frequency mode, said operating frequency varying when treating for said motion sickness in said variable operating frequency mode; and
a means for measuring said user's head velocity movement up to three axes in any combination, said means for controlling being responsive to changes in said user's head velocity movement for varying said operating frequency in said variable frequency operating mode, and wherein said three axes comprise a x-axis (pitch), y-axis (yaw), and z-axis (roll).

33. The eyewear of claim 32, wherein said means for measuring measures said movement in at least two axes in any combination.

34. The eyewear of claim 33, wherein said at least two axes comprise said y-axis (yaw) and said x-axis (pitch).

* * * * *